United States Patent [19]

Brander et al.

[11] Patent Number: 4,729,451

[45] Date of Patent: Mar. 8, 1988

[54] RECEIVER SUSPENSION AND ACOUSTIC PORTING SYSTEM

[75] Inventors: Richard Brander, Cicero; Timothy A. Daneliuk, Chicago, both of Ill.

[73] Assignee: Beltone Electronics, Corporation, Chicago, Ill.

[21] Appl. No.: 879,263

[22] Filed: Jun. 27, 1986

Related U.S. Application Data

[63] Continuation of Ser. No. 615,517, May 30, 1984, abandoned.

[51] Int. Cl.4 .......................... A61B 7/02; H04R 25/02

[52] U.S. Cl. .................................... 181/130; 181/135; 381/68.6; 381/69; 381/205

[58] Field of Search ............................... 181/130, 135; 179/107 E; 381/68.6, 69, 69.2, 205

[56] References Cited

U.S. PATENT DOCUMENTS

| | | | |
|---|---|---|---|
| 3,448,224 | 6/1969 | Giller | 381/68.6 |
| 3,865,998 | 2/1975 | Weiss et al. | 381/68.6 |
| 4,532,649 | 7/1985 | Bellagiore | 179/107 E |
| 4,588,867 | 5/1986 | Konomi | 179/107 E |
| 4,617,429 | 10/1986 | Bellagiore | 381/68.6 |

*Primary Examiner*—Benjamin R. Fuller

*Attorney, Agent, or Firm*—Allegretti, Newitt, Witcoff & McAndrews, Ltd.

[57] ABSTRACT

A system for suspending a receiver in a hearing aid and acoustically linking the receiver with the region external to the hearing aid. A shaped mandrel is placed inside the shell of the hearing aid and a liquid material is poured into the shell. The liquid material polymerizes to form an elastomer that is around the mandrel and in contact with the shell. The mandrel is then removed from the shell, leaving a receiver cavity and sound channel. A receiver is inserted into the receiver cavity. The receiver cavity holds the receiver, and the sound channel grippingly engages an acoustic output port on the receiver. The sound channel extends between the receiver and shell, acoustically linking the receiver with the external region.

1 Claim, 6 Drawing Figures

30

RECEIVER SUSPENSION AND ACOUSTIC PORTING SYSTEM

This is a continuation of U.S. application Ser. No. 615,517, filed May 30, 1984, now abandoned.

BACKGROUND OF THE INVENTION

The present invention relates generally to the internal structure of a hearing aid and more particularly to a suspension and acoustic porting system for the receiver of an "in the ear" or "canal" type hearing aid.

Such hearing aids include a shell that holds the components of the hearing aid and rests within the external ear of a user. The components include a receiver and a sound channel interconnecting the receiver and shell. Electrical signals are sent to the receiver by other components within the hearing aid, and the receiver responsively creates sound. The sound travels from the receiver, through the sound channel and shell, to the user's ear canal and ear drum.

Many presently available systems to physically support the receiver within the hearing aid shell and acoustically interconnect it to the exterior of the hearing aid are poorly adapted to meet the special requirements of an "in the ear" or "canal" type hearing aid. Since such hearing aids rest within the external ear, the shell of the hearing aid must be small. Accordingly, the components within the shell, including the receiver and sound channel, must be arranged as compactly as possible.

The receiver must, of course, be mounted securely within the hearing aid shell. However, the support system must also allow the receiver to be easily and quickly removed for repair or replacement.

To further ensure the proper operation of the receiver, the support system should allow the receiver to interconnect tightly with the sound channel. In this way, substantially all sound emitted by the receiver will travel into the sound channel and the ear drum of the user, rather than being dispersed within the hearing aid itself.

In addition, receivers are typically delicate instruments. A support system should cushion the receiver against shocks, such as would occur, for example, if the hearing aid is accidentally dropped on the floor.

The support structure should also isolate the receiver from mechanical and acoustical feedback so that the receiver will not transmit spurious, unwanted sound or vibration to the hearing aid microphone. Such feedback would cause distortion in the sound heard by the hearing aid user. In extreme cases, such feedback could lead to oscillation (causing the hearing aid receiver to emit an unpleasant "squeal.")

Further, the support system should be easy and inexpensive to manufacture. Consequently, the price of hearing aids to consumer may be lower.

SUMMARY OF THE INVENTION

In a principal aspect, the present invention is a receiver suspension and acoustic porting system for a hearing aid. The hearing aid includes an external shell having an output port and defining an interior area of the shell. Within the hearing aid is a receiver which includes an acoustic output port.

Compliant material is affixed to, and extends inwardly from, the interior surface of the shell. The compliant material defines a receiver cavity, or opening, within the shell for accepting a hearing aid receiver. Thus, the receiver is supported by the compliant material and substantially vibrationally isolated from the shell.

In addition, the compliant material defines an elongate sound channel extending from the acoustic output port of the receiver to the output port in the shell of the hearing aid. The sound channel grippingly engages the acoustic output port, acoustically linking the receiver with the output port in the shell of the hearing aid.

In another aspect of the invention, a plurality of ribs extend into the receiver opening. The ribs enhance the compliance of the receiver suspension to further reduce vibration transmission.

According to yet another aspect of the present invention, a suspension and acoustic porting system may be formed for a hearing aid. As before, the hearing aid includes a shell having an output port.

According to the present invention, a mandrel is formed having a main body and an elongate protrusion. Next, the mandrel is inserted into the hearing aid shell until the elongate protrusion extends through the output port and the main body of the mandrel lies within the shell.

A polymerizable liquid material is then poured into the shell around the mandrel. The liquid material is allowed to polymerize to form an elastomer around the mandrel and in contact with the shell. Thereafter, the mandrel is removed from the shell, leaving a receiver cavity formed by the main body of the mandrel and a sound channel formed by the elongate protrusion of the mandrel. The receiver is then inserted into the receiver opening formed by the resilient mold material and the receiver sound port is grippingly engaged by the sound channel.

Accordingly, an object of the present invention is an improved receiver suspension and acoustic porting system for a hearing aid. Another object is a system that lowers the level of mechanical and acoustic feedack transmitted by the receiver. Still further, an object is a system that more advantageously uses the space available within a hearing aid shell to hold a receiver and sound channel.

A further object is a system for supporting a hearing aid receiver that offers a greater cushioning effect to protect the receiver from physical damage. Still another object is a system that allows the receiver to be more easily and quickly removed from the hearing aid. Yet another object is a system that allows the receiver to be more tightly interconnected to the sound channel of the hearing aid.

An additional object of the present invention is an improved receiver suspension and acoustic porting system that more securely holds the receiver in a predetermined position. Yet still another object is a system that is easier and less expensive to manufacture.

BRIEF DESCRIPTION OF THE DRAWING

A preferred embodiment of the present invention is described herein with reference to the drawing wherein.

DETAILED DESCRIPTION OF A PREFERRED EMBODIMENT

Figure 1:
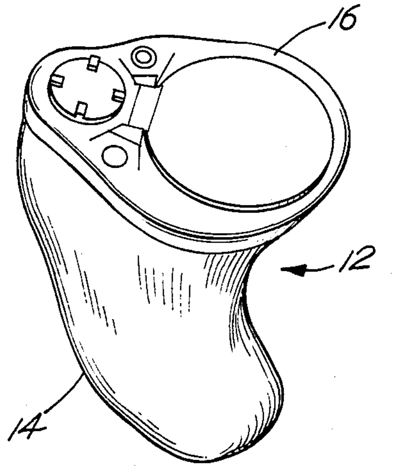
FIG. 1 is a perspective view of a typical hearing aid employing a preferred embodiment of the present invention.

Referring to FIGS. 1-6, a preferred embodiment of the present invention is shown as a receiver suspension and acoustic porting system, generally designated 10, for a hearing aid. A typical canal type hearing aid 12 is shown in FIG. 1 for illustrative purposes.

Figure 2:
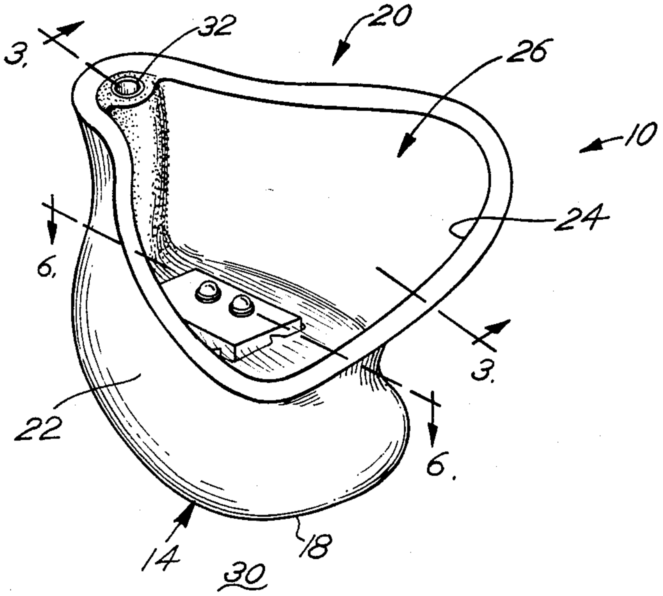
FIG. 2 is a perspective view the preferred embodiment used in the hearing aid of FIG. 1.

The typical hearing aid 12 includes an acrylic shell 14 and faceplate 16. As shown in FIG. 2, the shell 14 includes a closed end 18, an open end 20 to which the faceplate 16 may be attached, and a side wall 22 between the open and closed ends 18, 20.

Figure 3:
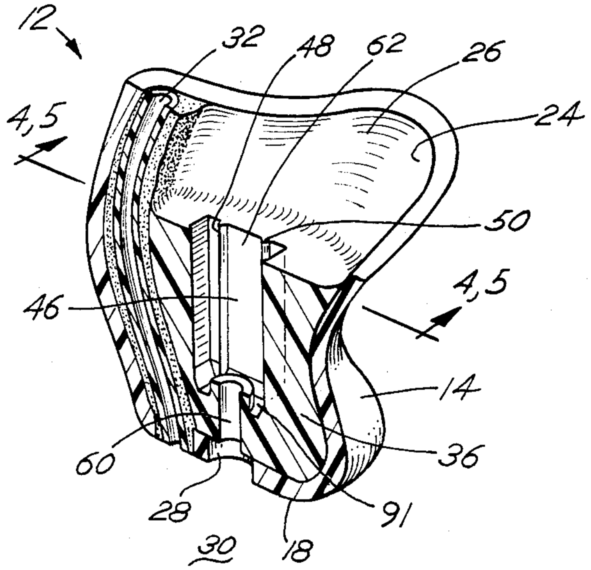
FIG. 3 is a perspective view of a cross-section of the preferred embodiment of the present invention, taken substantially along the line 3—3 in FIG. 2.

The closed end 18 and side wall 22 cooperatively define an interior surface 24 of the shell 14 and an interior space 26 within the shell 14, adjacent the interior surface 24. In addition, as shown in FIG. 3, the closed end 18 of the shell 14 defines an output port 28. The output port 28 is roughly cylindrical in shape, with a diameter of approximately 0.11 inch, and extends from the interior surface 24 of the shell 14 to a region 30 external to the hearing aid 12.

Figure 5:
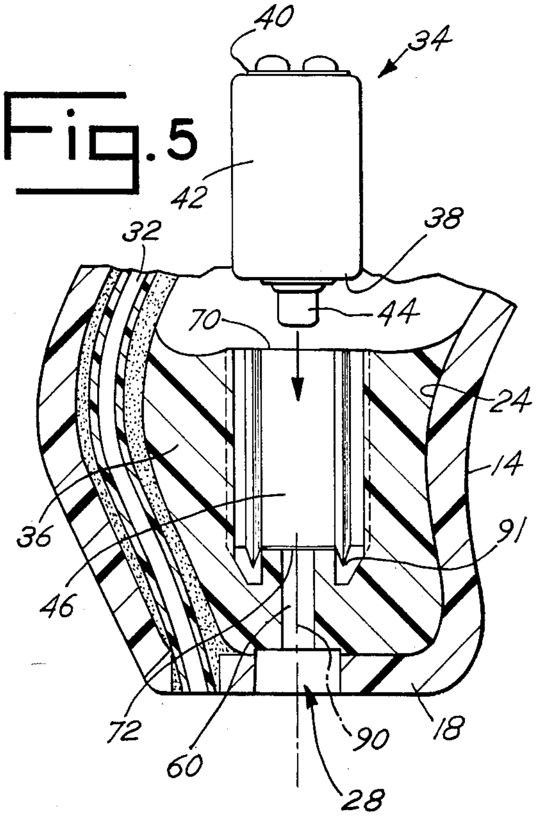
FIG. 5 is an enlarged cross-sectional view of the receiver cavity and sound channel of the preferred embodiment shown in FIG. 3, taken substantially along the line 5—5, with receiver about the receiver cavity.

The interior space 26 of the shell 14 houses most components of the hearing aid 12, including a vent 32, microphone (not shown), receiver 34, and compliant suspension 36 for the receiver 34. (FIGS. 2 and 5.) For clarity, only the vent 32, receiver 34, and compliant suspension 36 are shown within the shell 14 of FIG. 2.

The vent 32 extends from the closed end 18 of the shell 14 to the cover 16. Thus, any buildup of air pressure within the ear canal of the user (not shown) caused by inserting the hearing aid 12 into the ear will be released via the vent 32. The vent 32 also modifies the acoustic response of the hearing aid 12.

As shown in FIG. 5, the receiver 34 includes first and second end walls 38, 40 and four side walls 42 therebetween. The first and second end walls 38, 40 are separated by approximately 0.250 inch. The first end wall 38 includes a cylindrical acoustic output port 44 that protrudes from the receiver 34 approximately 0.060 inch. The acoustic output port 44 defines a diameter of approximately 0.055 inch.

The compliant suspension 36 within the shell 14 of the hearing aid 12 is substantially comprised of an elastomer material, such as Room Temperature Vulcanizing silicone rubber ("RTV"). Applicants have found, for example, that the RTV sold by the General Electric Company and the Dow Corning Corporation to be satisfactory material for use with the present invention.

The RTV is affixed to the interior surface 24 of the shell 14 and extends inwardly. Inside the shell 14, however, the compliant suspension 36 defines a receiver cavity or opening 46, for accepting the receiver 34, six ribs 48, 50, 52, 54, 56, 58 which extend into the receiver opening 46, and an elongate sound channel 60. See FIGS. 5 and 6.

Figure 6:
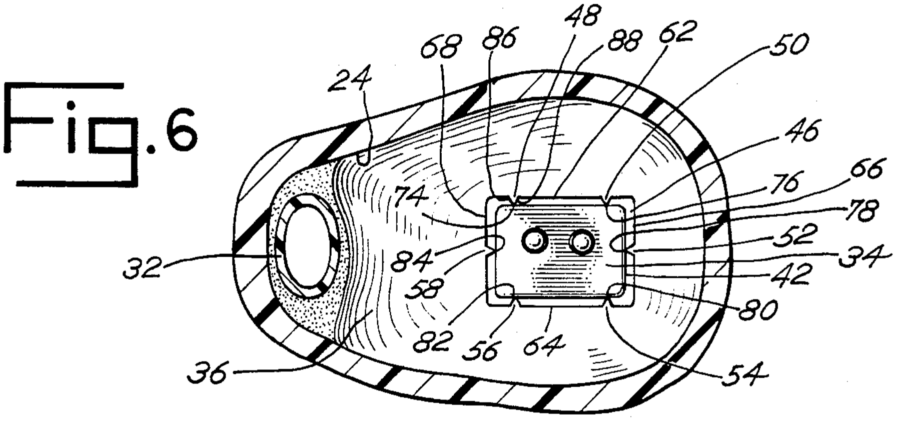
FIG. 6 is a cross-sectional view of the preferred embodiment shown in FIG. 2, taken substantially along line 6—6, with the receiver within the receiver cavity.

The receiver cavity 46, shown in FIGS. 5 and 6, includes four substantially closed sides 62, 64, 66, 68, a substantially closed end 72 and an open end 70. The two opposing sides 62, 64 are separated by approximately 0.140 inch. The two other opposing sides 66, 68 are separated by approximately 0.190 inch.

The open end 70 of the receiver cavity 46 is closer to the open end 20 of the shell 14 than is the substantially closed end 72 of the receiver cavity 46. Thus, the open end 70 may accept the receiver 34 as it is inserted into the shell 14. The substantially closed end 72 of the receiver cavity 46 is closer to the closed end 18 of the shell 14 than is the open end 70 of the receiver cavity 46. The open and substantially closed ends 70, 72 are separated by approximately 0.2 to 0.3 inch.

Each of the six ribs includes an outermost edge, respectively designated 74, 76, 78, 80, 82, 84. Moreover, the ribs 48–58 are substantially identical to each other, so that the description of the one rib 48 is set out below to illustrate the structure of each of the other ribs 50–58.

The rib 48 is an extension of the rest of the RTV making up the compliant suspension 36 in the shell 14 and extends approximately 0.010 inch into the receiver cavity 46 from the rest of the compliant suspension 36. The rib 48 includes two substantially planar sides 86, 88 which meet each other, at the outer edge 74, at an angle of approximately 45°. As shown in FIG. 3, the rib 48 extends along the closed side 62 of the receiver cavity 46.

As shown in FIG. 6, the ribs 52, 58 are located substantially in the middle, respectively, of the closed sides 66, 68. The outer edges 74, 76, 80, 82 of each of the ribs 48, 50, 54, 56 lie approximately 0.053 inch from one of the closed sides 66, 68.

The elongate sound channel 60 extends from the substantially closed end 72 of the receiver cavity 46 to the output port 28 in the shell 14. The sound channel 60 defines a centerline 90 between the receiver opening 46 and the output port 28 of the hearing aid 12. The centerline 90 is in the very middle of the sound channel 60 and is shown, in the preferred embodiment, as being straight. The cross section (not shown) of the sound channel 60 is perpendicular to the centerline 90 and has a predetermined, circular shape. The diameter of the circular shape is approximately 0.050 inch.

Consequently, the receiver 34 may be inserted into the receiver opening 46 as shown in FIG. 5. The side wall 42 of the receiver 34 defines a shape substantially similar to the shape defined by the outer edges 74–84 of the six ribs 48–58 extending into the receiver opening 46. When fully inserted into the receiver cavity 46, the sound channel 60 grippingly engages the acoustic output port 44 of the receiver 34.

Since the diameter of the acoustic output port 44 is slightly larger than the diameter of the sound channel 60, the sound channel 60 expands slightly to accept the acoustic output port 44. Consequently, the sound channel 60 tightly seals about the acoustic output port 44, helping to ensure that sound emitted through the acoustic output port 44 is not dispersed through the hearing aid 12. Rather, substantially all of the sound emitted from the acoustic output port 44 of the receiver 34 travels through the sound channel 60 and output port 28 of the hearing aid 12, into the user's ear canal and ear drum (not shown).

Moreover, the ribs 48–58 support and cushion the receiver 34. If the hearing aid 12 is subjected to a shock, the receiver 34 may press against the compliant suspension 36, which in turn, may deform to protect the receiver 34 from damage. After the shock has stopped, the cushion 36 will substantially resume its previous shape and restore the receiver 34 to its previous location within the shell 14.

The ribs 48–58 form a very compliant suspension for receiver 34. In addition, relief space 91 is provided around the sound channel 60 adjacent to the acoustic output port 44 of the receiver 34 to increase compliance in this area. As a result, the compliant suspension 36 acts as an efficient vibration isolator to prevent vibrations produced by the driven receiver 34 from being transmitted to the hearing aid microphone as undesired feedback. Such feedback could cause signal distortion or oscillation.

Although the sound channel 60 engages the acoustic output port 44 and the ribs 48–58 may engage the side walls 42 of the receiver 34, the cushion 36 is resilient. Thus, the receiver 34 may be pulled from the receiver opening 46 after insertion.

Figure 4:
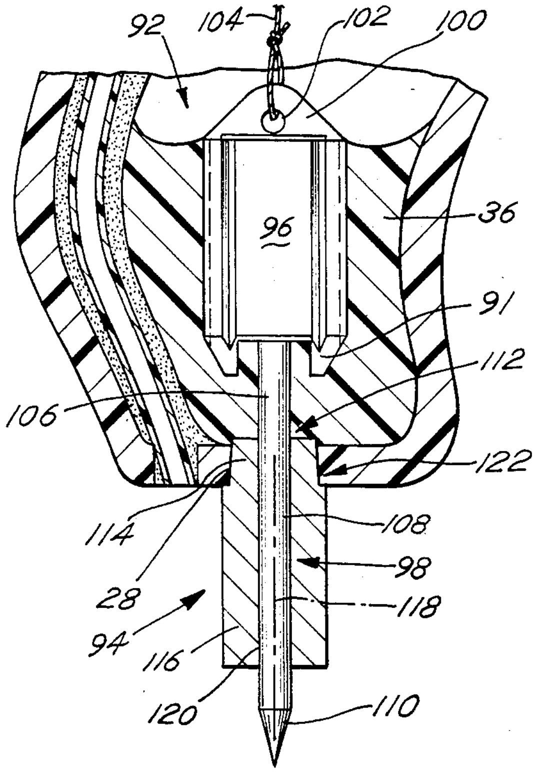
FIG. 4 is an enlarged, cross-sectional view of the receiver cavity and sound channel of the preferred embodiment shown in FIG. 3, taken substantially along the line 4—4, with the mandrel within the receiver cavity.

The suspension and acoustic port system 10 may be easily and inexpensively formed. In the preferred embodiment, a mandrel 92 and a support block 94 are constructed. (FIG. 4.) The mandrel 92 and support block 94 are both made of polyethylene and constructed using the injection molding process. The mandrel 92 includes a main body 96 and an cylindrical elongate protrusion 98 extending therefrom.

The main body 96 of the mandrel 92 defines a shape substantially the same as the previously-described receiver opening 46. In addition, the main body 96 includes an upper flange 100. The upper flange 100 includes a 0.034 inch diameter hole 102 therethrough and a wire 104 extending through the hole 102.

The elongate protrusion 98 of the mandrel 92 includes an upper region 106 and lower region 108. The upper region 106 of the elongate protrusion 98 is directly interconnected to the main body 96 and has a diameter of approximately 0.050 inch. The lower region 108 is directly interconnected to the upper region 106 on one end and includes a pointed tip 110 on the other end. Except for the pointed tip 110, which is roughly 0.07 inch long, the lower region 108 has a diameter of only about 0.044 inch. The junction of the larger diameter upper region 106 and smaller diameter lower region 108 of the elongate protrusion 98 defines a shoulder 112.

The support block 94 is roughly cylindrical in shape, defining upper and lower regions 114, 116, a longitudinal axis 118, and central aperture 120. (FIG. 4.) The lower region 116 defines an outside diameter of approximately 0.140 inch. As shown in FIG. 4, the upper region 114 is slightly tapered and has an average outside diameter of approximately 0.108 inch. The junction of the larger diameter lower region 116 and smaller diameter upper region 118 defines a shoulder 122.

The central aperture 120 has a diameter of approximately 0.046 inch and extends along the longitudinal axis 118. Thus, the central aperture 120 traverses both the upper and lower regions 114, 116 of the support block 94.

As shown in FIG. 5, once formed, the mandrel 92 may be lowered, by holding onto the wire 104, into the interior area 26 of the shell 14 of the hearing aid 12. The elongate protrusion 98 enters the shell 14 first, followed by the main body 96 of the mandrel 92. The pointed tip 110 may then be inserted into the output port 28 of hearing aid 12, to guide the elongate protrusion 98 therethrough as the mandrel 92 is lowered into the shell 14.

Thereafter, the central aperture 120 of the support block 94 may be placed about the elongate protrusion 98. As shown in FIG. 4, the support block 94 may then be pushed into the shell 14 until the shoulder 122 of the support block 94 rests against the shell 14.

Next, the mandrel 92 may be furthered lowered until the shoulder 112 between the upper and lower regions 106, 108 of the elongate protrusion 98 abuts the upper region 114 of the support block 94. When the mandrel 92 has thus been properly positioned, the liquid RTV may be poured into the shell 14, about the main body 96 and upper region 106 of the elongate protrusion 98. See FIG. 4. In such a condition, the main body 96 of the mandrel 92 is approximately 0.2 to 0.3 inch deep in the RTV.

The RTV will vulcanize, or cure, and thus change from a liquid to an elastic solid. Such a process will occur if the RTV is left at room temperature. Applicants have noted, however, that the curing process will be completed faster, within two or three hours, if the RTV is placed in an oven (not shown) which has a temperature that has been elevated to approximately 150° Farenheit (66° Celcius). During this process, the RTV forms about the main body 96 and elongate protrusion 98 of the mandrel 92 to form, respectively, the receiver opening 46 and sound channel 60.

After the curing process is completed, the mandrel 92 may be taken out of the shell 14 by pulling on the wire 104. The support block 94 may then also be pulled away from the shell 14.

Upon removing the mandrel 92 from the shell 14, the receiver 34 may be inserted therein. Moreover, it may be noted that the support block 94 substantially prevents the RTV from entering the output port 28 of the hearing aid 12. Thus, the output port 28 is kept substantially empty, and an apparatus may be inserted in the output port 28, for example, to prevent wax (not shown) from entering the sound channel 60 and receiver 34. Such an apparatus is disclosed, for example, in a copending application Ser. No. 584,451 filed on Feb. 29, 1984 by Richard Brander and Mark F. Stanton for a Wax Guard System.

A preferred embodiment of the present invention has been described herein. It is to be understood, however, that changes and modifications can be made without departing from the true scope and spirit of the present invention. This true scope and spirit are defined by the following claims and their equivalents, to be interpreted in light of the foregoing specification.

What is claimed is:

1. A receiver suspension and acoustic porting system for a hearing aid, said hearing aid including a receiver having an acoustic output port, comprising, in combination:

an external shell including an inward wall, an open end, and a side wall therebetween, said inward wall defining an output port therethrough, said inward and side walls defining both an interior surface and an interior area of said shell, pliable suspension means within said interior area, substantially affixed to said interior surface of said shell and extending inwardly therefrom, for supporting said receiver, said pliable suspension means being made of a pliant material and defining first and second voids and a plurality of pliable rib means, said first void defining a receiver chamber for accepting said receiver, said second void defining an elongate output passageway extending from said acoustic output port of said receiver at one end to said acoustic output port of said shell at another end, said one end of said elongate output passageway defining coupling means for grippingly engaging said acoustic output port of said receiver, whereby said acoustic output port is acoustically linked to said output passageway and said output port of said shell, and said pliable rib means extending into said receiver chamber, for supporting said receiver, whereby said receiver is cushioned by said pliable suspension means and ribs and substantially acoustically isolated from said shell.

* * * * *